United States Patent [19]

Keller

[11] Patent Number: 4,869,118
[45] Date of Patent: Sep. 26, 1989

[54] WATER RETRIEVER

[76] Inventor: Marcella M. Keller, 732 Morton Ave., Kewanee, Ill. 61443

[21] Appl. No.: 294,778

[22] Filed: Jan. 9, 1989

[51] Int. Cl.⁴ ............................................. G01N 1/12
[52] U.S. Cl. .................................................. 73/864.63
[58] Field of Search ........... 73/864.51, 864.63, 864.64, 73/864.65, 864.66, 864.67

[56] References Cited

U.S. PATENT DOCUMENTS

| | | | |
|---|---|---|---|
| 38,427 | 5/1863 | Tagliabue | 73/864.63 |
| 1,864,472 | 6/1932 | Riebeling | 73/864.63 |
| 2,189,238 | 2/1940 | Benjamin | 73/864.63 |
| 2,501,895 | 3/1950 | Gayle | 248/146 |
| 2,598,183 | 5/1952 | Long et al. | 73/864.66 |
| 3,118,307 | 1/1964 | Pettersson | 73/864.66 |
| 3,459,048 | 8/1969 | Bicknell | 73/864.63 |
| 3,675,491 | 7/1972 | Guillet | 73/864.63 |
| 3,714,830 | 2/1973 | Keir | 73/864.63 |
| 3,968,696 | 7/1976 | Rosenblum | 73/864.63 |
| 4,760,747 | 8/1988 | Fackler | 73/864.63 |

FOREIGN PATENT DOCUMENTS

| | | | |
|---|---|---|---|
| 153799 | 11/1920 | United Kingdom | 248/146 |
| 961081 | 6/1964 | United Kingdom | 248/318 |
| 2032885 | 5/1980 | United Kingdom | 73/864.63 |

Primary Examiner—Robert R. Raevis
Attorney, Agent, or Firm—Robert O. Richardson

[57] ABSTRACT

A water sample retriever for sampling water at a predetermined depth below the water surface comprising a covered container, a rigid longitudinal member for placing the container at said predetermined depth, and a vertical movable lift for removing the cover to admit water into the container for conveyance to the surface for testing.

1 Claim, 2 Drawing Sheets

U.S. Patent  Sep. 26, 1989  Sheet 1 of 2  4,869,118
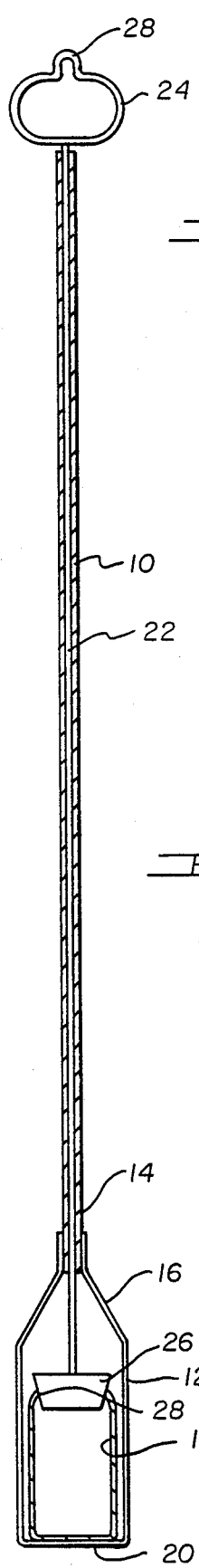
Fig_1
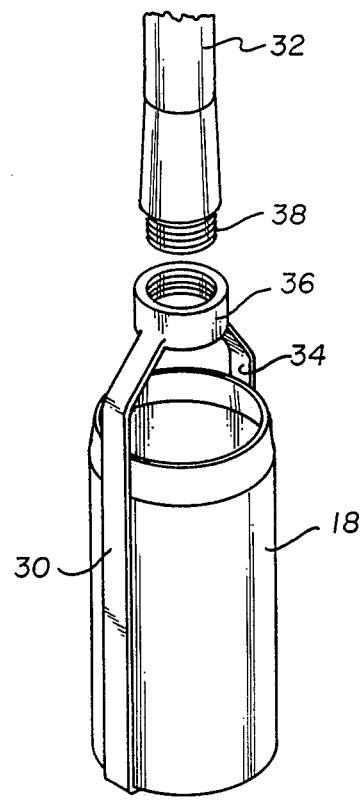
Fig_2
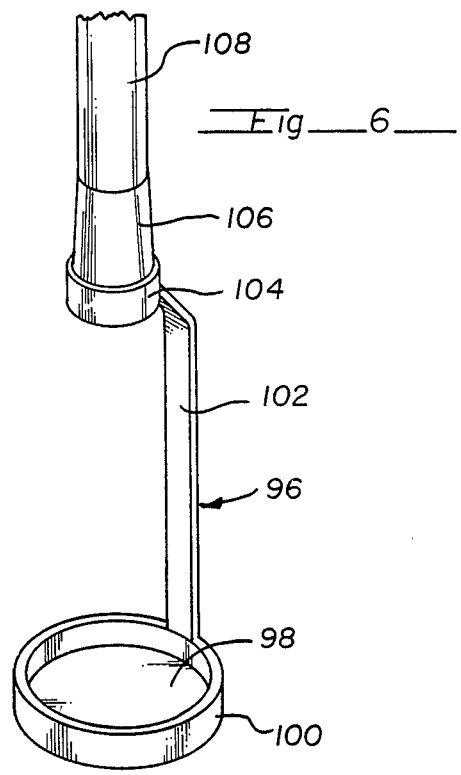
Fig_6

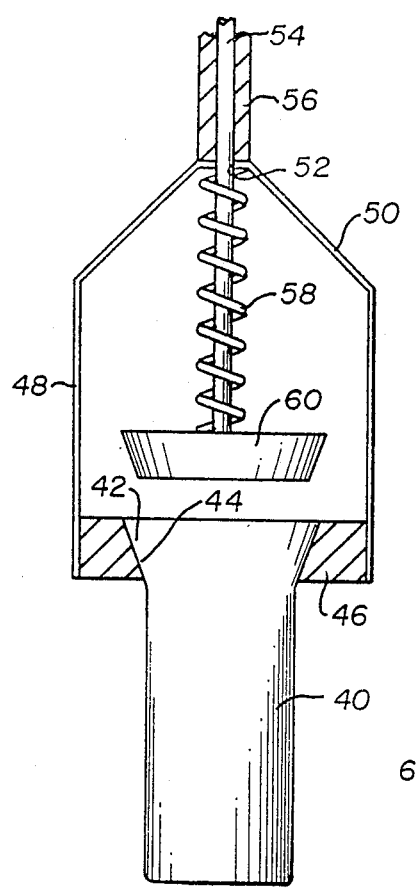
Fig_3
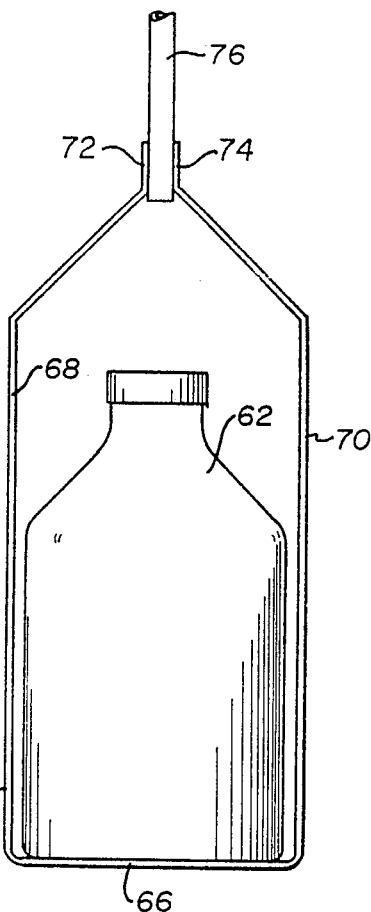
Fig_4
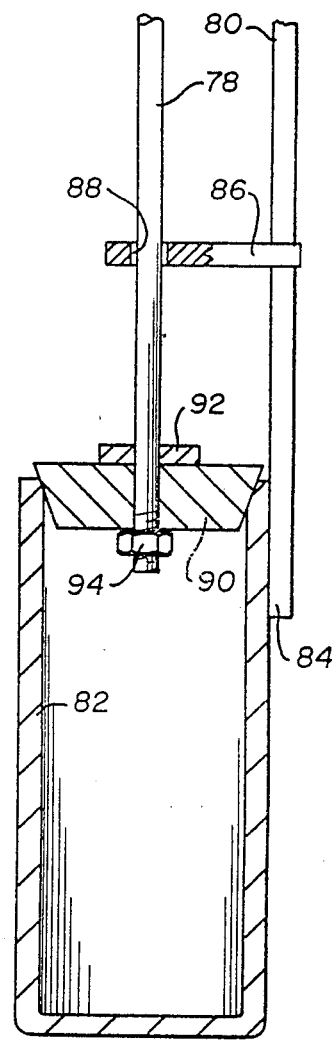
Fig_5
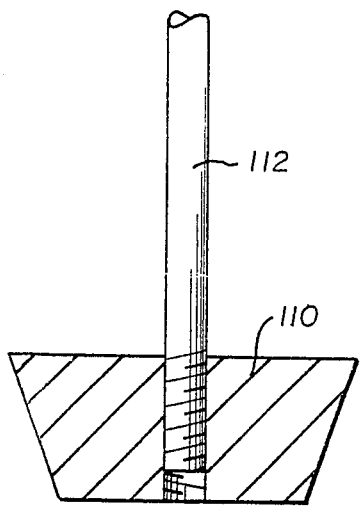
Fig_7
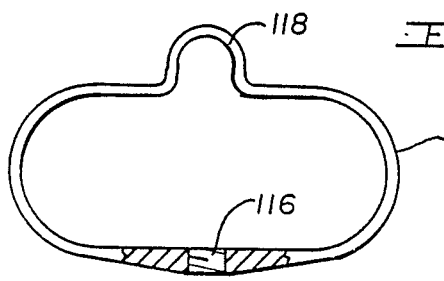
Fig_8
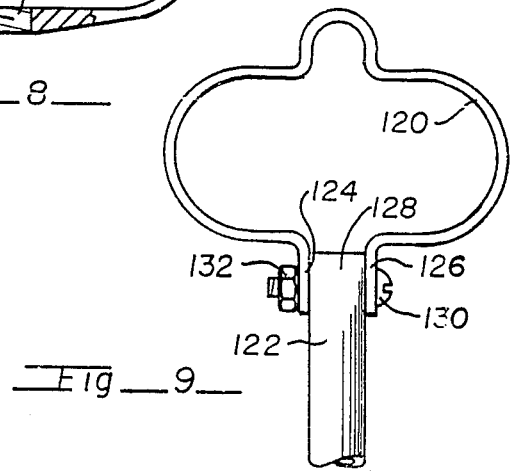
Fig_9

WATER RETRIEVER

BACKGROUND OF THE INVENTION

There are millions of spa and swimming pools throughout the world. These and other bodies of water must be tested periodically for purity, chemical and/or contamination content. In testing of the water in swimming pools, a sample of water about 18 inches below the water surface is recommended for greater accuracy in the test results. Greater accuracy in the test results will often indicate that fewer, cheaper and less potent chemicals need be added to correct the chemical deficiency or contamination excess in the water.

In collecting a water sample 18 inches below the water surface, the person taking the sample uses a container and kneels or stoops so that the container may be dipped down into the water to the 18 inch below surface level. There the water may be scooped up in the container and brought to the surface for analysis. This past procedure requires the tester to stoop or kneel to dip up a container of water from 18 inches below the water surface. Kneeling down on the rough cement deck can be hard on arthritic knees, can cause wear and tear on the retriever's slacks or hose and can be hard on the back. The water is not always at a comfortable swimming temperature and the wet dipping hand and arm can become very cold and uncomfortable. Jacket, coat and shirt sleeves have to be rolled up above the elbow to avoid getting wet. This wrinkles the material. If the garmets get wet, they have to be changed. The hand and arm has to be dried with a towel after the dipping operation is completed. All of these inconveniences and annoyances leads one to conclude that there must be a better way of retrieving water samples from below the water surface.

SUMMARY OF THE PRESENT INVENTION

In accordance with the present invention a closed empty container is placed at the proper desired water depth. In this requirement it is 18 inches below the water surface. When the container is at the proper level, it is opened to permit it to be filled with a water sample at this desired level. Preferably the container is then closed, although this is not always a requirement, prior to retrieving it for testing.

Briefly the equipment needed to perform the above operation consists of a rigid tube or rod with a water container attached to, or supported by, its lower end. The water container has a cover to prevent surface water filling the container as it is lowered into the water to the recommended 18 inch depth. A vertically moveable lift means is provided for removing the cover while the container is submerged and, at the option of the sampler, the cover may be replaced on the container before its recovery.

BRIEF DESCRIPTION OF THE DRAWINGS

FIG. 1 is a vertical view of the water retriever of the present invention with the immersing tube and container shown in section, FIG. 2 is a partial view in perspective showing how in one form the immersing tube and container holder are connected, FIG. 3 is a partial side view of another embodiment with the immersing tube and holder shown in section, FIG. 4 is a partial side view of an alternate form of connection of the immersing tube and container holder, FIG. 5 is a partial side view partly in section of an alternate embodiment, FIG. 6 is a partial view in perspective of an alternate container holder, FIG. 7 is a partial sectional view showing one form of attachment of the container lid to the remote cover remover, FIG. 8 is an elevational view partly in section of a removeable handle, and FIG. 9 is a partial side view of another form of handle connection to the remote cover remover.

DETAILED DESCRIPTION OF PREFERRED EMBODIMENTS

Reference is made to FIG. 1 wherein there is shown one form of water retriever of the present invention comprising an immersing tube 10 with a container support 12 attached at its lower end 14 by support arms 16. A container 18 to receive water is positioned on the base 20 of the support 12.

Extending through immersing tube 10 is a remote cover remover rod 22. A handle 24 fastened at the top of the rod permits its vertical movement within the tube 10. At the bottom of rod 22 is mounted a lid or container cover 26. This lid or cover 26 is of such size as to fit snuggly over the top opening 28 to keep water out of the container 18 until the lid is removed. The support arms 16 are long enough relative to the height of the container 18, and the cover remover rod 22 extends downwardly sufficiently from the lower end 14 of the tube 10, that there is ample room to pull the lid 26 upwardly without any structural interference. This vertical movement is done by the operator grasping the top of tube 10 with one hand and pulling handle 24 upwardly with the other.

While handle 24 is generally of a squashed oval shape large enough to receive two or three fingers, it has an upper loop 28 that makes it convenient to store it on a nail on the pool fence or wall of a nearby structure.

FIG. 2 shows container 18 held by container support 30 removeably fastenable to immersing tube 32. Support 30 has support arms 34 that terminate at the top in a threaded receiver 36. Tube 32 has male threads 38 at its lower end to threadably engage receiver 36. For convenience the container lid and cover remover rod are not shown.

FIG. 3 shows another embodiment wherein container 40 has an enlarged upper opening with outwardly extending lips 42 which are received by and rest on the inverse conical tapered wall of opening 44 in base 46 of the container support 48. An inverted U-shaped support arm 50 has both ends attached to the base 46 and has an aperture 52 at its upper mid-portion for passage of the cover removal rod 54 therethrough. The lower end of immersing tube 56 is attached to support arm 50 around the aperture 52. A spring 58 over the end of rod 54 bears against container stopper 60 and the undersurface of support arm around aperture 52. This spring causes the stopper 60 to bear down onto and into the lips 42 of container 40. In this manner container 40 is always closed except when stopper 60 is raised by rod 54.

In FIG. 4 the container 62 has a smaller neck and upper opening. The container support 64 has an integral base 66 and support arms 68, 70 whose upper ends 72, 74 terminate and are fastened to the immersing tube 76.

FIG. 5 shows an alternate embodiment wherein the cover remover rod 78 does not move vertically within an immersing tube but exteriorily of an immersing rod 80. The immersing rod 80 has the liquid container 82 affixed to its lower end 84. Above the container a guide 86 is mounted on rod 80. It has an aperture 88 therein to receive the cover removing rod 78 for vertical movement. The lower end of rod 78 had the container cover 90 removeably mounted thereon between collar 92 and nut 94 threadably attached to the rod.

Container support 96 shown in FIG. 6 has a base 98 with a circular wall 100 from which a single rigid arm 102 extends upwardly. This arm terminates in a threaded receiver 104 for fastening to the lower end 106 of immersing tube 108.

FIG. 7 shows a removeable stopper 110 threadedly engageable with cover removable rod 112. Not only may various sizes of stoppers be used to accommodate containers with varied size openings, their removability make it easier to install rod 112 within its immersing tube. After the rod is inserted into the tube, the stopper can be threadedly engaged to the end of the rod.

FIG. 8 is a side view of a handle 114. This handle has a threaded aperture 116 for fastening the handle to the upper end of the container cover removal rod. It also has an upper loop 118 to facilitate storage when hanging the handle over a mounting screw or nail on a wall or post near the water source.

FIG. 9 shows another way of fastening handle 120 to the cover lift rod 122. Handle 120 has a pair of legs 124, 126 which straddle upper end 128 of rod 122. Bolt 103 passes through suitable apertures in legs 124, 126 and end 128 and is held by nut 132.

From the foregoing description it is obvious to one skilled in the art that other modifications and variations are possible and it is to be understood that these alternate versions are to be considered as part of my invention as set forth in the following claims.

What I claim is:

1. A water retriever comprising:
    a container having an opening at the top thereof,
    a cover for said container,
    a rigid longitudinal member container placement means for placing said container at a predetermined depth below the surface of a water body to be tested,
    a vertically movable lift member cover removal rod extending upwardly from said cover for removing said cover from said container to permit water at said predetermined depth to fill said container for conveyance to the water surface for testing, said container placement means having an inverted U-shaped support arm attached thereto at the lower end thereof, and
    a container supporting base attached to the lower ends of said support arm, said support arm having an aperture at its upper mid-portion for passage of said cover removal rod therethrough, said base having an opening therein within an inverse conical tapered wall, said container having an enlarged upper opening with outwardly extending lips which are received by and which rest on said wall of said opening to support said container thereby.

* * * * *